(12) United States Patent
Watanabe et al.

(10) Patent No.: US 9,176,063 B2
(45) Date of Patent: Nov. 3, 2015

(54) MODIFIED FLUORESCENT PROTEIN

(75) Inventors: Tomonobu Watanabe, Osaka (JP); Keiko Yoshizawa, Nara (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/884,520

(22) PCT Filed: Nov. 10, 2011

(86) PCT No.: PCT/JP2011/075932
§ 371 (c)(1),
(2), (4) Date: May 9, 2013

(87) PCT Pub. No.: WO2012/063897
PCT Pub. Date: May 18, 2012

(65) Prior Publication Data
US 2013/0220021 A1    Aug. 29, 2013

(30) Foreign Application Priority Data
Nov. 12, 2010  (JP) .................................. 2010-254016

(51) Int. Cl.
*G01L 11/02* (2006.01)
*G01N 21/64* (2006.01)
*C07K 14/435* (2006.01)

(52) U.S. Cl.
CPC ...... *G01N 21/6486* (2013.01); *C07K 14/43504* (2013.01); *C07K 14/43595* (2013.01); *G01L 11/02* (2013.01); *C07K 2319/60* (2013.01)

(58) Field of Classification Search
None
See application file for complete search history.

(56) References Cited

U.S. PATENT DOCUMENTS

| 2003/0004306 A1 | 1/2003 | Miyawaki et al. |
| 2003/0017538 A1 | 1/2003 | Miyawaki et al. |

FOREIGN PATENT DOCUMENTS

| JP | 2002-253261 A | 9/2002 |
| JP | 2002-369690 A | 12/2002 |
| JP | 2011-188821 A | 9/2011 |

OTHER PUBLICATIONS

Baird et al. "Circular permutation and receptor insertion within green fluorescent proteins." Proc Natl Acad Sci U S A. (Sep. 1999); 96(20): pp. 11241-11246.*
Verkhusha et al., "Effect of high pressure and reversed micelles on the fluorescent proteins," Biochimica et Biophysica Acta, 1622: 192-195 (2003).
Horner et al., "Mechanical stimulation by osmotic and hydrostatic pressure activates Drosophila oocytes in vitro in acalcium-dependent manner," Developmental Biology, 316: 100-109 (2008).
Baird et al., "Circular permutation and receptor insertion within green fluorescent proteins," Proc, Natl. Acad. Sci, 96: 11241-11246 (1999).
Watanabe et al., "Developments of the force sensitive fluorescent probe using fluorescent proteins," Biophysical Society of Japan, S103.1-P261 (2009).
Watanabe et al., "Measurement analysis for explaining life phenomenon," SAKIGAKE CREST Meeting of Report Results, 1-4 (2010).
GenBank, AC048266, EYPF, 2009.
Search Report issued in corresponding International Patent Application No. PCT/JP2011/075932 dated Dec. 6, 2011.
Watanabe et al., "Glycine Insertion Makes Yellow Fluorescent Protein Sensitive to Hydrostatic Pressure," PLOS One, 8: e73212 (2013).
Watanabe et al., "Intracellular Pressure Measurement by using Pressure Sensitive Yellow Fluorescent Protein," Biophysical Journal, 102: 419a (2012).
Extended European Search Report issued in corresponding European patent Application No. 11839408.9 dated Mar. 6, 2014.

* cited by examiner

*Primary Examiner* — Thaian N Ton
*Assistant Examiner* — Titilayo Moloye
(74) *Attorney, Agent, or Firm* — Morgan, Lewis & Bockius LLP

(57) ABSTRACT

Provided is a modified fluorescent protein which enables the detection of a power applied to a liquid where the fluorescent protein exists. A modified fluorescent protein, wherein a peptide linker is inserted into a position homologous to the position between the 144th and 145th amino acids in the amino acid sequence of a wild type fluorescent protein from jellyfish or a fluorescent protein derived from said wild type fluorescent protein, characterized in that the fluorescence properties of said modified fluorescent protein change depending on a change in a pressure that is applied to a liquid where said modified fluorescent protein exists.

17 Claims, 5 Drawing Sheets

//PAGE 1

MODIFIED FLUORESCENT PROTEIN

TECHNICAL FIELD

The present invention relates to a modified fluorescent protein.

BACKGROUND ART

A fluorescent protein, for example, a green fluorescent protein having an amino acid sequence represented by SEQ ID NO: 6 of a sequence listing is generally used as a material for fluorescently labeling a protein in basic research and application research. Fluorescent labeling with a fluorescent protein enables the observation of localization and movement of a protein under an optical microscope. Further, a fluorescent protein that responds to environment, such as cytoplasmic pH and calcium concentration, has also been created by genetic engineering modification (Patent Documents 1 and 2). The fluorescent protein capable of responding to a cytoplasmic environment change is a very potential tool for checking life phenomenon.

On the other hand, conventionally, it has been suggested that there is a strong correlation between the pressure in a living body and the life phenomenon, as is found in the fact that the shape of a tissue which is being generated is determined by a pressure in a cytoplasm.

PRIOR ART DOCUMENTS

Patent Document 1: JP 2002-253261 A
Patent Document 2: JP 2002-369690 A

DISCLOSURE OF INVENTION

Problem to be Solved by the Invention

However, there is no technology capable of measuring a pressure in a living body, and hence, the above-mentioned hypothesis is still to be verified. It is considered that a technology capable of visualizing a pressure in a living body will greatly develop biological study. In particular, if a pressure in a living body can be visualized with a fluorescent protein, the pressure can be measured non-invasively, that is, without damaging a living sample such as a cell or a living body.

The present invention provides a modified fluorescent protein allowing a pressure in a liquid to be measured.

Means for Solving Problem

The present invention relates to a modified fluorescent protein comprising a peptide linker inserted into a position homologous to a position between 144th and 145th amino acids in an amino acid sequence of a wild type fluorescent protein isolated from jellyfish or a fluorescent protein derived from the wild type fluorescent protein, wherein fluorescence properties of the modified fluorescent protein change depending on a change in pressure applied to a liquid in which the modified fluorescent protein exists.

Effects of the Invention

The fluorescence properties of the modified fluorescent protein of the present invention change depending on a change in pressure applied to a liquid in which the modified fluorescent protein of the present invention exists, and preferably, the change in pressure and the fluorescent intensity exhibit a positive correlation. Therefore, the modified fluorescent protein of the present invention is capable of visualizing a change in pressure in a living body and enables the pressure to be measured with time based on a change in fluorescence non-invasively, that is, without damaging a living sample such as a cell or a living body. Further, a change in pressure applied to a liquid in which the modified fluorescent protein of the present invention exists can be detected easily.

BRIEF DESCRIPTION OF DRAWINGS

FIG. 1 is a schematic diagram of YFP and insertion mutants each created by inserting a peptide linker between 144th and 145th positions of the YFP.

[FIG. 2] FIG. 2 is graphs showing absorption wavelength spectra (black lines) of YFP and insertion mutants of the YFP, and fluorescent wavelength spectra (gray line) obtained when excited with a laser having a wavelength of 488 nanometers.

FIG. 3 is graphs showing pressure dependence of the YFP (FIG. 3A), the YFP-1G (FIG. 3B), and the YFP-3G (FIG. 3C).

FIG. 4 is graphs respectively showing a relationship between the pressure and the fluorescent peak wavelength (a) and a relationship (b) between the pressure and the fluorescent intensity at a fluorescent peak wavelength (b) in the YFP, the YFP-1G, and the YFP-3G.

FIG. 5 is a graph obtained by plotting a change ratio of fluorescent intensity when a pressure applied to a YFP-3G aqueous solution is changed from 0 MPa to a predetermined pressure.

FIG. 6 is a graph showing results obtained by calculating a change in pressure applied to a liquid in which the modified fluorescent protein of the present invention exists from the graph of FIG. 5, based on a change in fluorescent intensity measured for the YFP3G in the aqueous solution. Each line is obtained by making attempts respectively.

FIG. 7 is a graph showing a relationship between the pressure in the YFP, the YFP-1G, and the YFP-3G and the fluorescent intensity at a fluorescent peak wavelength.

FIG. 8 is a graph showing a relationship between the pressure in GFP, GFP-1G, and GFP-3G and the fluorescent intensity at a fluorescent peak wavelength.

FIG. 9 is a graph showing a relationship between the pressure in CFP, CFP-1G, and CFP-3G and the fluorescent intensity at a fluorescent peak wavelength.

[FIG. 10]

DESCRIPTION OF THE INVENTION

Figure 1:
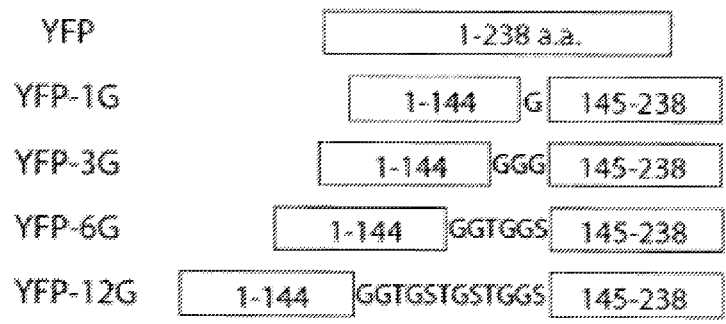
[FIG. 1]
Figure 2A:
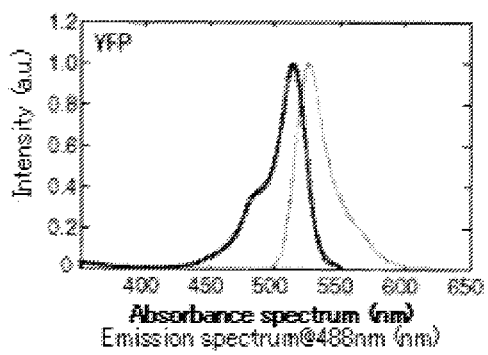
(FIG. 2A) shows the result of wild type YFP.
Figure 2C:
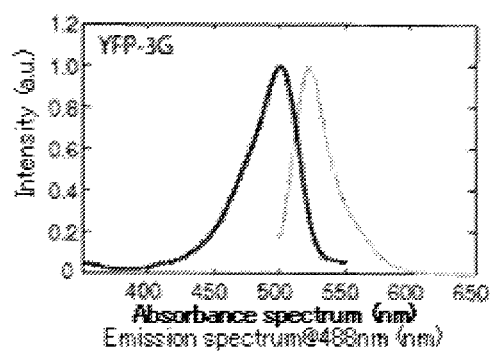
(FIG. 2C) the result of YFP-3G.
Figure 2B:
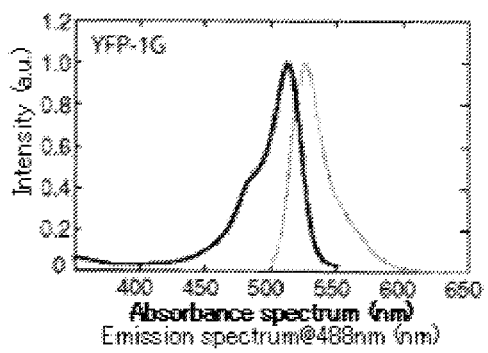
(FIG. 2B) the result of YFP-1G.
Figure 2D:
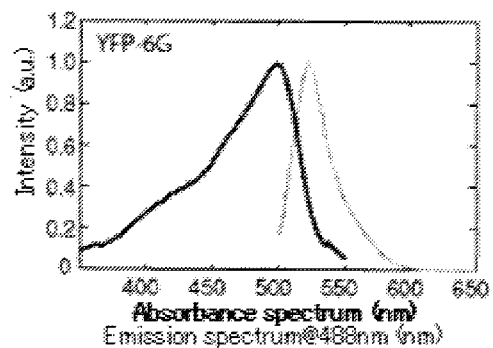
(FIG. 2D) the result of YFP-6G.

A fluorescent protein is a protein having a cylindrical structure called a "β-can structure". There is a chromophore composed of three amino acid residues in the β-can structure, and the chromophore sensitively responds to a proton configuration caused by the surrounding β-can structure. The present invention is based on the finding that, by inserting a peptide linker into a part of a fluorescent protein, more specifically, a loop closest to the chromophore, a modified fluorescent protein can be obtained in which the fluorescence properties change depending on a change in pressure applied to a liquid in which the fluorescent protein exists, and preferably, a pressure applied to the liquid in which the fluorescent protein exists and fluorescent intensity exhibit a positive correlation.

That is, in one aspect, the present invention relates to a modified fluorescent protein (hereinafter, sometimes, referred to as "modified fluorescent protein of the present invention") in which a peptide linker is inserted into a position homologous to the position between the 144th and 145th amino acids in the amino acid sequence of a wild type fluorescent protein isolated from jellyfish or a fluorescent protein derived from the wild type fluorescent protein, characterized in that the fluorescence properties of the modified fluorescent protein change depending on a change in pressure applied to a liquid in which the modified fluorescent protein exists.

Although a mechanism in which the fluorescence properties of the modified fluorescent protein of the present invention change depending on a change in pressure applied to a liquid in which the modified fluorescent protein of the present invention exists is not clear, the following interpretation can be considered. That is, when a peptide linker is inserted into a part of a fluorescent protein, more specifically, a loop closest to a chromophore, a β-can structure located close to the chromophore in the fluorescent protein is distorted, which allows water in a solvent to enter the chromophore. The chromophore interacts with water to change fluorescence properties. That is, the following is considered: a pressure applied to a liquid in which the modified fluorescent protein of the present invention exists increases to change the behavior of water in the chromophore, with the result that a fluorescent wavelength of light emitted from the chromophore changes, and/or fluorescent intensity increases. It should be noted that the present invention may not be construed only based on the above-mentioned mechanism.

No fluorescent protein allowing a pressure in a solvent to be measured has been reported. Further, in regenerative medicine, it is becoming clear gradually that a pressure is important for determining the shape of a tissue. However, there is no technology capable of measuring a pressure in a cell, and hence, further finding has not been obtained. The modified fluorescent protein of the present invention can be expressed in a cell by a simple method such as gene transfer. Therefore, the modified fluorescent protein of the present invention may become a tool that is useful and applicable, for a number of biological researchers. For example, in study of deep-sea creatures, it is necessary to check a relationship between the pressure and the life phenomenon, and hence, the modified fluorescent protein of the present invention may become a tool that is also very important for the study of deep-sea creatures.

[Fluorescent Protein]

The term "fluorescent protein" as used herein refers to a protein emitting light when irradiated with excitation light. Although the fluorescent protein is not particularly limited, there may be given *Galaxea fascicularis, Fungia* sp., *Montipora*, sp. and the like isolated from coral; *Halcurias* sp. L and the like isolated from sea anemone; and *Aequorea victoria* and the like isolated from jellyfish, as a material for the modified fluorescent protein. Preferably, there may be given those which are obtained by using, as a material, a wild type fluorescent protein isolated from jellyfish or a fluorescent protein derived from the wild type fluorescent protein. In the present invention, the term "wild type fluorescent protein isolated from jellyfish" refers to a fluorescent protein isolated from jellyfish of 238 (full-length) amino acid residues, and preferably refers to a green fluorescent protein (GFP; 238 (full-length) amino acid residues, GenBank Accession No. AAA27722, SEQ ID NO: 6 of a sequence listing) isolated from jellyfish (*Aequorea Victoria*). Further, the term "fluorescent protein derived from the wild type fluorescent protein" as used herein includes a mutant fluorescent protein derived from the GFP, and preferably includes fluorescent proteins such as YFP, CFP, EGFP, EYFP, and ECFP. Hereinafter, in the present invention, the "wild type fluorescent protein isolated from jellyfish or fluorescent protein derived from the wild type fluorescent protein" is sometimes referred to simply as "fluorescent protein". As a sequence of the YFP, there may be given an amino acid sequence of SEQ ID NO: 1 of 238 amino acid residues, and as a sequence of the CFP, there may be given an amino acid sequence of SEQ ID NO: 7 of 238 amino acid residues. However, in the present invention, the YFP and the CFP are not limited to the above-mentioned sequences. For example, the sequences of the YFP and the CFP may include those which include substitutions, additions, deletions, or insertions of one or a plurality of amino acid residues in the vicinity of an N-terminal or a C-terminal for the purpose of cloning or TAG labeling in a range not influencing the function as a fluorescent protein, and those which do not have an amino acid sequence length of 238 amino acid residues because of the substitutions, additions, deletions, or insertions. It is appropriate that the insertion site of a linker in this case (that is, a loop closest to a chromophore) is set to a position homologous to the position between the 144th and 145th amino acids in the amino acid sequence of the wild type fluorescent protein. The fluorescent protein in the present invention can be easily obtained as, for example, a commercially available product in a form of not only a protein but also a polynucleotide encoding the fluorescent protein or a vector capable of expressing the fluorescent protein. As the fluorescent protein in the present invention, the YFP and the EYFP (in particular, represented by an amino acid sequence of SEQ ID NO: 1) are preferred, which are fluorescent proteins with tyrosine substituted for threonine at amino acid residue 203 of the green fluorescent protein. The reason for this is as follows. In the YFP and the EYFP, a chromophore (65-67 residues) and a phenol ring of tyrosine at amino acid residue 203 interact with each other electronically, and hence, the emission characteristics of the YFP and the EYFP are expected to change sensitively, compared with the GFP.

[Peptide Linker]

The term "peptide linker" as used herein refers to an amino acid sequence to be inserted into a fluorescent protein. The number of amino acids of the peptide linker is preferably 1 or more from the viewpoint of maintaining sensitivity to a pressure and fluorescent intensity. Further, from the same viewpoint, the number of amino acids of the peptide linker is preferably 4 or less, more preferably 3 or less. Thus, the number of amino acids of the peptide linker is preferably 1 to 4, more preferably 1 to 3. Further, it is preferred that amino acid residues of the peptide linker include glycine, and it is more preferred that all the amino acid residues are glycine, from the viewpoint of maintaining sensitivity to a pressure and fluorescent intensity.

The insertion position of the peptide linker is a loop closest to a chromophore of the fluorescent protein, preferably the position between 144th and 145th positions of an amino acid sequence of a fluorescent protein, more preferably a site homologous to the position between the 144th and 145th amino acids in the wild type fluorescent protein, that is, the green fluorescent protein (GFP; GenBank Accession No. AAA27722, SEQ ID NO: 6) of 238 (full-length) amino acid residues. Even in the case where the peptide linker is to be inserted into a fluorescent protein that does not have an amino acid sequence length of 238 amino acid residues, those skilled in the art would be able to specify an insertion site easily by general alignment, visual comparison of sequences, or the like.

[Fluorescence Properties that Change Depending on Change in Pressure]

The term "fluorescence properties" as used herein includes an excitation wavelength, a fluorescent wavelength, spectra thereof, and fluorescent intensity. In the modified fluorescent protein of the present invention with a peptide linker inserted thereto, at least one of the fluorescence properties changes depending on a change in pressure applied to a liquid in which the modified fluorescent protein of the present invention exists, and preferably, at least fluorescent intensity changes in a positive correlation depending on a change in pressure applied to a liquid in which the modified fluorescent protein of the present invention exists. The expression "fluorescent intensity changes in a positive correlation depending on a change in pressure applied to a liquid in which the modified fluorescent protein of the present invention changes" means the following. When a pressure applied to a liquid in which the modified fluorescent protein of the present invention exists increases, fluorescent intensity increases, and when a pressure applied to a liquid in which the modified fluorescent protein of the present invention exists decreases, fluorescent intensity decreases. A pressure applied to a liquid in which the modified fluorescent protein of the present invention exists preferably more than 0 MPa and 1,000 MPa or less, more preferably more than 0 MPa and 500 MPa or less, still more preferably more than 0 MPa and 300 MPa or less from the viewpoint of maintaining sensitivity of a pressure and fluorescent intensity.

[Method for Producing a Modified Fluorescent Protein of the Present Invention]

The modified fluorescent protein of the present invention can be produced easily by a known method, for example, by cloning a modified DNA in which a DNA of a basic sequence encoding a peptide linker is inserted into a site homologous to the position between the 144th and 145th amino acids in an amino acid sequence of a wild type fluorescent protein isolated from jellyfish or a fluorescent protein derived from the wild type fluorescent protein in a DNA encoding the wild type fluorescent protein isolated from jellyfish or the fluorescent protein derived from the wild type fluorescent protein, and expressing the cloned modified DNA appropriately. Handling including a method for purifying the modified fluorescent protein of the present invention can be the same as that of the fluorescent protein subjected to modification. Further, in the case where the modified fluorescent protein of the present invention is expressed in a living body, there is a method for cloning a DNA encoding the modified fluorescent protein of the present invention to an appropriate expression vector, and transferring the vector to an intended cell or living body. It should be noted that the modified fluorescent protein of the present invention is not limited to its production method, cloning method, expression method, and gene-transfer method.

Thus, in another aspect, the present invention relates to a vector (hereinafter, sometimes referred to as "vector of the present invention") encoding the modified fluorescent protein of the present invention. The vector of the present invention may be an expression vector for expressing the modified fluorescent protein of the present invention. In the expression vector, an expression system is not particularly limited, and whether the expression system is a prokaryote or a eukaryote does not matter. Thus, in still another aspect, the present invention relates to living organisms excluding cells or human beings gene-transferred with the modified fluorescent protein of the present invention. Further, the present invention also relates to a kit including the vector of the present invention, containing a reagent required for gene transfer, cells, an instruction manual, etc., as needed.

[Fusion form with an Internal Standard Fluorescent Protein]

A pressure applied to a liquid in which the modified fluorescent protein of the present invention exists can also be measured by combining the modified fluorescent protein of the present invention with a conventional fluorescent protein, using the conventional fluorescent protein as an internal standard whose fluorescence properties do not change with respect to a pressure, and comparing the fluorescence properties of both the proteins. In the case of using a fluorescent protein as an internal standard, it is preferred that the modified fluorescent protein of the present invention be different from the internal standard protein in fluorescence properties, and it is preferred that the modified fluorescent protein of the present invention be different from the internal standard protein in excitation wavelength and spectrum thereof. Further, from the viewpoint of regulating expression amounts of both the proteins to enhance sensitivity, a fusion protein form in which the modified fluorescent protein of the present invention is fused with the internal standard protein is preferred. Thus, in still another aspect, the present invention relates to a fusion fluorescent protein (hereinafter, sometimes referred to as "fusion fluorescent protein of the present invention") in which the modified fluorescent protein of the present invention is fused with a fluorescent protein having an excitation spectrum different from that of the modified fluorescent protein.

In the fusion fluorescent protein of the present invention, the modified fluorescent protein of the present invention and the internal standard fluorescent protein may be fused with each other through a linker. Those skilled in the art would be able to produce the fusion fluorescent protein of the present invention easily, for example, by cloning a DNA fragment encoding the modified fluorescent protein of the present invention to a vector of a known fluorescent protein. Thus, in still another aspect, the present invention relates to a vector encoding the fusion fluorescent protein of the present invention. The vector may be an expression vector for expressing the fusion fluorescent protein of the present invention. In the expression vector, an expression system is not particularly limited, and whether the expression system is a prokaryote or a eukaryote does not matter. Thus, in still another aspect, the present invention relates to living organisms excluding cells or human beings gene-transferred with the fusion fluorescent protein of the present invention. Still further, the present invention can relate to a kit including the vector, containing a reagent required for gene transfer, cells, an instruction manual, etc., as needed.

[Pressure Measurement Method]

In still another aspect, the present invention relates to a method for detecting a change in pressure or a pressure applied to a liquid in which the modified fluorescent protein/fusion fluorescent protein of the present invention exists, in which fluorescent intensity or a fluorescent wavelength of the fluorescent protein is detected.

The fluorescence properties of the modified fluorescent protein/fusion fluorescent protein of the present invention change depending on a pressure applied to a liquid in which the modified fluorescent protein/fusion fluorescent protein of the present invention exists. Therefore, for example, by allowing the modified fluorescent protein/fusion fluorescent protein to exist in a cell, a blood vessel, an embryo, or an aqueous solution, a change in pressure applied to any one of them can be detected. Further, by using an internal standard together or the fusion fluorescent protein of the present invention, a pressure can also be known in real time. The detection sensitivity of a pressure using the modified fluorescent protein/fusion fluorescent protein of the present invention can be set to, for example, 1.0 MPa to 0.1 MPa, preferably 0.8 MPa to 0.4 MPa, more preferably 0.7 MPa to 0.5 MPa. Further, a pressure that can be detected is, for example, more than 0 MPa and 1,000 MPa or less. From the viewpoint of the detection sensitivity, a lower limit of the pressure is preferably 0.001 MPa or more, more preferably 0.01 MPa or more, still more preferably 0.05 MPa or more, still more preferably an atmospheric pressure or more. Further, from the same viewpoint, an upper limit of the pressure is preferably 500 MPa or less, more preferably 100 MPa or less, still more preferably 10 MPa or less, still more preferably 1 MPa or less.

The modified fluorescent protein of the present invention can be applied, more specifically, to measurement of a change in osmotic pressure in a cell, measurement of a change in blood pressure, and measurement of a body internal pressure of deep-sea creatures, etc.

Hereinafter, the present invention will be described by way of examples with reference to the drawings.

EXAMPLES

[Insertion Mutant of YFP]

Insertion mutants were produced respectively by inserting a peptide linker between aspartic acid at amino acid residue 144 and tyrosine at amino acid residue 145 of a yellow fluorescent protein (YFP) of 238 (full-length) amino acid residues represented by SEQ ID NO: 1 of a sequence listing (FIG. 1). The inserted peptide linkers were G (mutant name: YFP-1G), GGG (mutant name: YFP-3G: SEQ ID NO: 2), GGTGGS (SEQ ID NO: 3) (mutant name: YFP-6G), GGTGGSGGTGGS (SEQ ID NO: 4) (mutant name: YFP-12G).

The YFP and the YFP mutants were expressed and purified by a conventional method. That is, a DNA plasmid encoding the YFP and the YFP mutants was transformed into E. coli, and the YFP and the YFP mutants were expressed in E. coli. The YFP and the YFP mutants were separated and purified from collected E. coli lysates (cytoplasm) by adding a FLAG tag (DYKDDDDK: SEQ ID NO: 5) to an N-terminal of the YFP and the YFP mutants.

[Comparison of Wavelength Characteristics]

An absorption wavelength spectrum and an emission wavelength spectrum of each of the insertion mutants produced as described above were checked. As a result, the absorption wavelength and the emission wavelength of the YFP shifted to a short wavelength owing to the insertion of glycine in accordance with the number of the inserted amino acid residues (FIG. 2). It is considered that the shift of the fluorescent wavelength revealed that the β-can structure changed owing to the insertion of glycine to change the environment on the periphery of a chromophore of the YFP. The fluorescent intensity of the YFP-6G and the YFP-12G decreases compared with the YFP, and hence, it is considered that the YFP-1G and the YFP-3G are more preferred as a fluorescent protein for detecting a pressure.

[Pressure Dependence of Wavelength Characteristics]

Figure 3A:
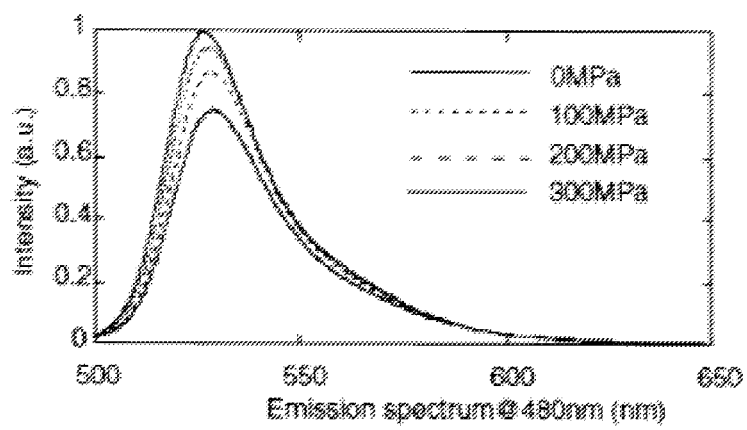
[FIG. 3]
Figure 3B:
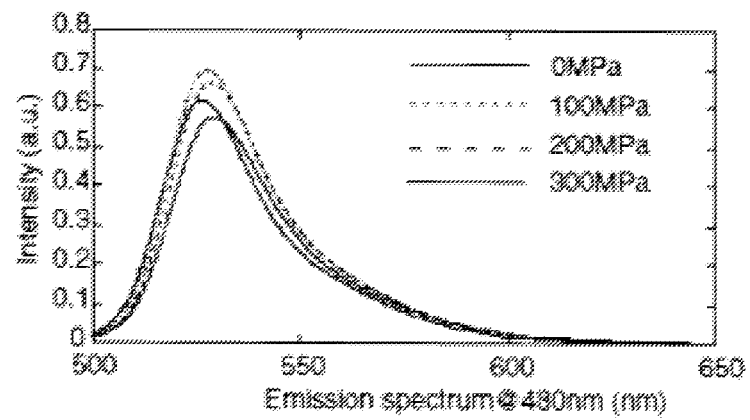
Figure 3C:
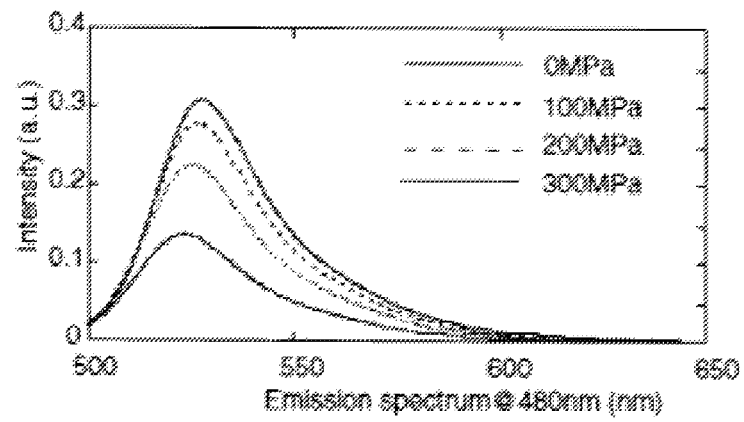

The pressure dependence of the YFP, the YFP-1G, and the YFP-3G were checked. Specifically, the pressure dependence was measured under the following conditions. FIG. 3(a) shows the results of the YFP, FIG. 3(b) shows the results of the YFP-1G, and FIG. 3(c) shows the results of the YFP-3G.

[Measurement Condition of Pressure Dependence]

YFP and YFP mutants were prepared so as to be in a concentration of 0.1 to 0.3 mg/ml in a solution of 20 mM of Hepes-NaOH (pH 8.0). The absorbance was measured in a range of an absorption wavelength of 250 to 600 nm by an absorption spectrophotometer (Shimadzu UV-Vis Spectrophotometer UV-1650PC). The fluorescent intensity was measured in a fluorescent wavelength of 500 to 650 nm with an excitation wavelength being fixed to 488 nm by a fluorescence spectrophotometer (Shimadzu UV-Vis Spectrophotometer UV-1650PC).

The fluorescence properties under a pressure were measured through use of a fluorescence spectrophotometer (Shimadzu UV-Vis Spectrophotometer UV-1650PC), a high-pressure absorbance cell unit (PCI500, Syn Corporation), and a pressure pump (HP-500, Syn Corporation). The pressure was changed at a speed of about 5 MPa per second so as to avoid a change in temperature involved in a rapid change in pressure. One minute after the intended pressure was achieved, the excitation wavelength was fixed to 480 nm, and fluorescence properties were measured in a fluorescent wavelength of 500 to 650 nm. An experiment was performed all at room temperature (25° C.).

As shown in FIG. 3(a), as a pressure was applied to the YFP, the peak wavelength shifted to a long wavelength side and fluorescent intensity decreased. As shown in FIG. 3(b), as a pressure was applied to the YFP-1G, the peak wavelength shifted to a long wavelength side and fluorescent intensity increased until the pressure reached 200 MPa and then decreased. As shown in FIG. 3(c), as a pressure was applied to the YFP-3G, the peak wavelength shifted to a long wavelength side and fluorescent intensity increased. FIG. 4 is graphs each summarizing the foregoing results.

Figures 4A, 4B:
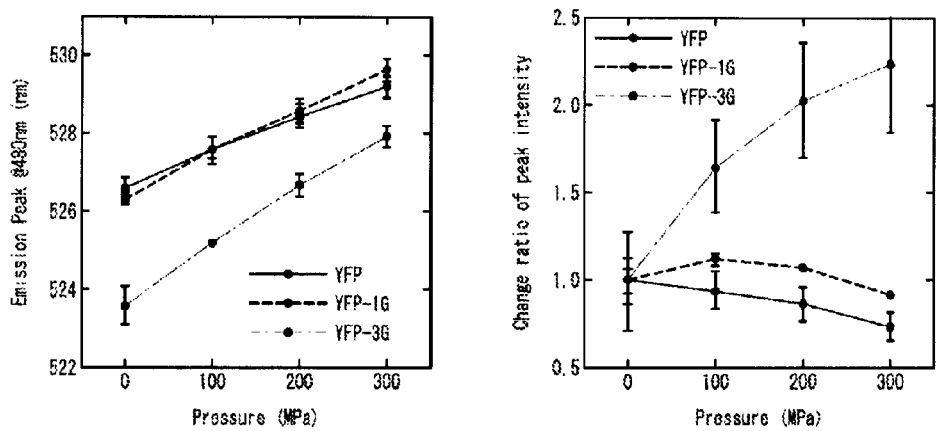
[FIG. 4]

As shown in FIG. 4(a), regarding the pressure dependence of a shift of the peak wavelength, no substantial difference was found among the YFP, the YFP-1G, and the YFP-3G. Further, as shown in FIG. 4(b), regarding the pressure dependence of a change in fluorescent intensity at a peak wavelength, a change ratio of the fluorescent intensity of the YFP under a pressure of 300 MPa was 0.75, whereas a change ratio of the fluorescent intensity of the YFP-3G under a pressure of 300 MPa was 2.4. Thus, it was revealed that the YFP-3G was greatly influenced by a pressure, compared with the YFP.

[Measurement of Change in Pressure from Change in Fluorescent Intensity]

Figure 5:
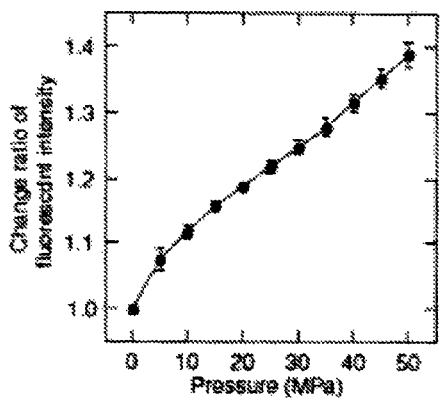
[FIG. 5]
Figure 6:
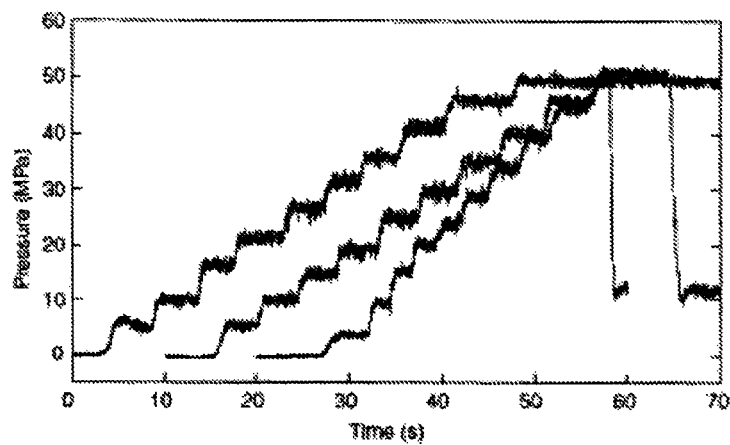
[FIG. 6]

A detailed correlation graph between the fluorescent intensity (515 to 535 nm) of the YFP-3G and the pressure (0 to 50 MPa) applied to a liquid in which the YFP-3G exists was created (FIG. 5). The graph of FIG. 5 was obtained by plotting a change ratio of fluorescent intensity when a pressure applied to an aqueous solution of the YFP-3G from 0 MPa to a predetermined pressure. As shown in FIG. 5, a change in pressure and a change in fluorescent intensity correlate with each other, and hence, a change in pressure applied to a liquid in which the YFP-3G exists can be estimated from the fluorescent intensity of the YFP-3G through use of FIG. 5 as a calibration table. FIG. 6 shows an example thereof.

FIG. 6 is a graph obtained by detecting fluorescent intensity of the YFP-3G when a pressure was applied each by 5 MPa to an aqueous solution of the YFP-3G at an interval of 5 seconds, and measuring a change in pressure with time from a change in the detected fluorescent intensity and the graph of FIG. 5. As shown in FIG. 6, a change in pressure was measured from a change in fluorescent intensity of the YFP-3G, and measurement accuracy thereof was 0.6 MPa.

Accordingly, the fluorescence properties of the modified fluorescent protein of the present invention change depending on a change in pressure applied to a liquid in which the YFP-3G exists, and hence, according to the present invention, it was shown that it is possible to measure a pressure applied to a liquid in which the modified fluorescent protein of the present invention exists.

[Production of GFP Mutants and CFP Mutants]

Insertion mutants were produced respectively by inserting a peptide linker between aspartic acid at amino acid residue 144 and tyrosine at amino acid residue 145 of each of a green fluorescent protein (GFP) and a cyan fluorescent protein (CFP) represented by amino acid sequences of SEQ ID NO: 6 and SEQ ID NO: 7 of a sequence listing. The inserted peptide linkers were G (mutant name: GFP-1G/CFP-1G or 1G insertion mutant) and GGS (mutant name: GFP-3G/CFP-3G or 3G insertion mutant). The GFP and GFP mutants, and the CFP and CFP mutants were expressed and purified in the same way as in the YFP and YFP mutants described above.

Figure 7:
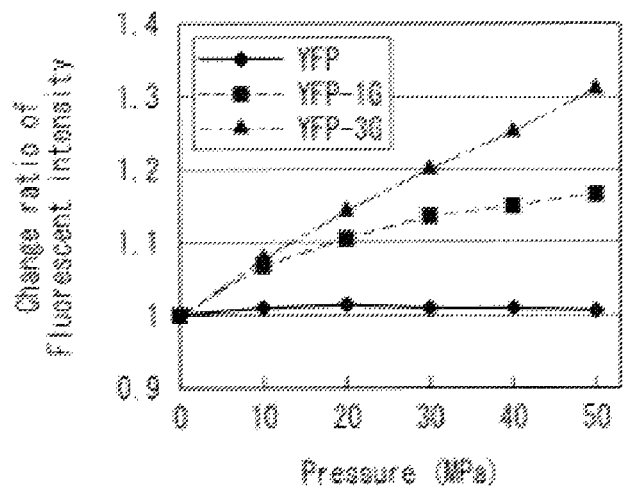
[FIG. 7]
Figure 8:
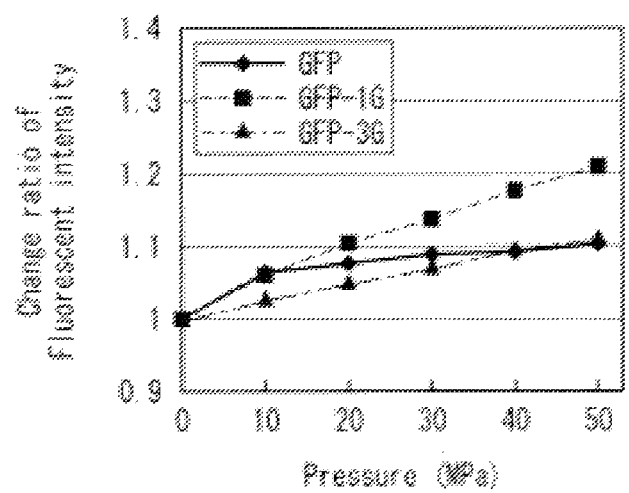
[FIG. 8]
Figure 9:
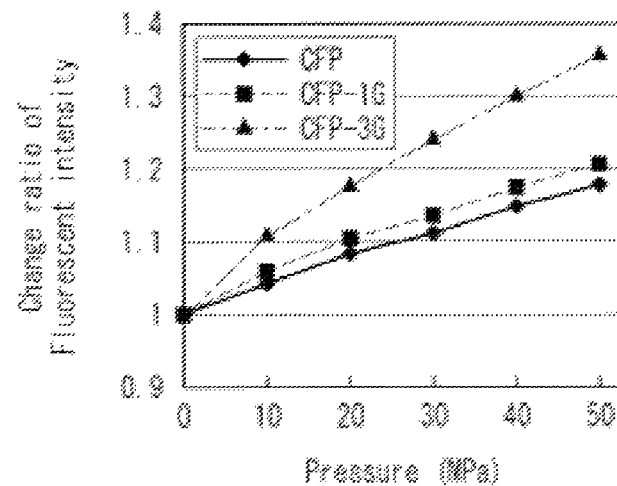
[FIG. 9]

The YFP, YFP-1G, YFP-3G, GFP, GFP-1G, GFP-3G, CFP, CFP-1G, and CFP-3G were measured for fluorescent intensity of a peak wavelength when a pressure applied to an atmospheric pressure was set to 0 to 50 MPa. The fluorescence properties under a pressure were measured in the same way as described above. FIGS. 7 to 9 respectively show the results of the YFP, the GFP, and the CFP.

As shown in FIGS. 7 to 9, the fluorescent intensities of both the 1G insertion mutant and the 3G insertion mutant exhibited a positive correlation with respect to an applied pressure of 0 to 50 MPa. As shown in FIG. 9, the fluorescent intensity of the CFP itself also exhibited a positive correlation with respect to the applied pressure, and the sensitivity to a pressure of the CFP was further enhanced by forming the CFP into the 1G insertion mutant and the 3G insertion mutant.

Figure 10A:
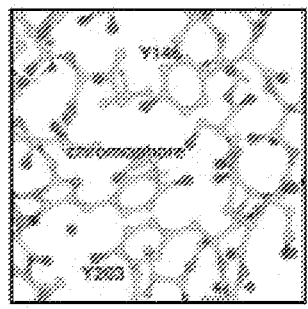
FIGS. 10A to 10C show three-dimensional structures of proteins on the periphery of chromophores of the YFP, the YFP-1G, and the YFP-3G.
Figure 10B:
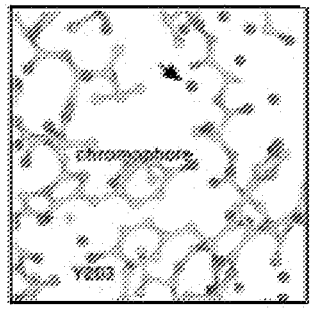
Figure 10C:
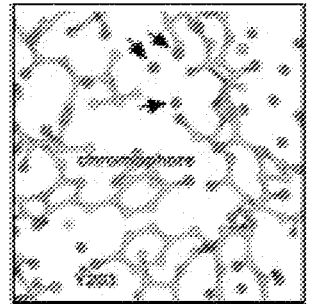

FIGS. 10A to 10C respectively show three-dimensional structures of the periphery of each chromophore of the YFP, the YFP-1G, and the YFP-3G. The structure of the YFP of FIG. 10A is cited from PDB data bank ID:3DQ7. The structural data of the YFP-1G of FIG. 10B and the YFP-3G of FIG. 10C were respectively registered as PDB data bank ID:3VGQ and 3VGR. In FIGS. 10B and 10C, arrows represent water molecules. FIG. 10 shows a state in which, when a linker is inserted into a loop closest to a chromophore, a β-can structure in a fluorescent protein is distorted, and thereby, water in a solvent enters the chromophore.

Industrial Applicability

According to the present invention, a change in pressure in a living body can be visualized, and the pressure can be measured with time based on a change in fluorescence non-invasively, that is, without damaging a living sample such as a cell or a living body. The present invention is useful for the fields of, for example, deep-sea investigation, cell biology, molecule imaging, medical and diagnostic drug, protein structure analysis, and the like.

| Sequence List Free Text | |
|---|---|
| SEQ ID NO: 1 | YFP (yellow fluorescent protein) |
| SEQ ID NO: 2 | An example of the modified protein of the present invention |
| SEQ ID NO: 3, 4 | Peptide linker |
| SEQ ID NO: 5 | FLAG tag |
| SEQ ID NO: 6 | GFP (green fluorescent protein) |
| SEQ ID NO: 7 | CFP (cyan fluorescent protein) |

The invention claimed is:

1. A method of detecting a pressure or a change in pressure applied to a liquid containing:
   A. a modified fluorescent protein (MFP),
      (1) wherein the MFP comprises a wild type green fluorescent protein of 238 amino acids isolated from jellyfish (WFP) modified with at least one amino acid inserted into a position corresponding to a position between 144 th and 145 th amino acids; or
      (2) wherein the MFP is a fluorescent protein derived from the WFP of A(1) that is further modified to be yellow fluorescent protein (YFP), cyan fluorescent protein (CFP), enhanced green fluorescent protein (EGFP), enhanced yellow fluorescent protein (EYFP), or enhanced cyan fluorescent protein (ECFP); or B. a fusion fluorescent protein (FFP), wherein the FFP is a fusion fluorescent protein in which the MFP is fused with a fluorescent protein having an excitation spectrum different from an excitation spectrum of the MFP, the method comprising:

detecting fluorescent intentsity of the MFP or FFP; and comparing the detected fluorescent intensity to (a) the fluorescent intensity of a control wild-type fluorescent protein or (b) the fluorescent intensity of the MFP or FFP when no pressure is applied, to determine the pressure or the change in pressure applied to the liquid containing the MFP or FFP, wherein when pressure applied to the liquid containing the MFP or FFP increases, the fluorescent intensity of the MFP or FFP increases, and when pressure applied to the liquid containing the MFP or FFP decreases, the fluorescent intensity of the MFP or FFP decreases.

2. The method according to claim 1, wherein the MFP comprises one to three amino acid(s) inserted into the position corresponding to the position between the 144 th and 145 th amino acids.

3. The method according to claim 1, wherein the inserted amino acid is glycine.

4. The method according to claim 1, wherein the MFP of A(2) is selected from the group consisting of YFP, CFP, and EYFP.

5. The method according to claim 1, wherein the MFP of A(2) is YFP.

6. The method according to claim 1, wherein MFP of A(2) is CFP.

7. The method according to claim 2, wherein the MFP of A(2) is selected from the group consisting of YFP, CFP, and EYFP.

8. The method according to claim 2, wherein the MFP of A(2) is YFP.

9. The method according to claim 2, wherein the MFP of A(2) is CFP.

10. The method according to claim 1, wherein the liquid contains the MFP of A(1).

11. The method according to claim 1, wherein the liquid contains the MFP of A(2).

12. The method according to claim 1, wherein the liquid contains the FFP.

13. The method according to claim 1, wherein the MFP of A(2) comprises an amino acid sequence of SEQ ID NO: 1.

14. The method according to claim 1, wherein the MFP of A(2) comprises an amino acid sequence of SEQ ID NO: 7.

15. The method according to claim 1, wherein the WFP comprises an amino acid sequence of SEQ ID NO: 6.

16. The method according to claim 1, wherein the detected fluorescent intensity is compared to (a) the fluorescent intensity of the control wild-type fluorescent protein.

17. The method according to claim 1, wherein the detected fluorescent intensity is compared to the fluorescent intensity of (b) the fluorescent intensity of the MFP or FFP when no pressure is applied.

* * * * *

SEQUENCE LISTING

```
<160> NUMBER OF SEQ ID NOS: 7

<210> SEQ ID NO 1
<211> LENGTH: 238
<212> TYPE: PRT
<213> ORGANISM: Artificial Sequence
<220> FEATURE:
<223> OTHER INFORMATION: EYFP (yellow fluorescent protein)

<400> SEQUENCE: 1

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140
```

```
Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Tyr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys
225                 230                 235
```

<210> SEQ ID NO 2
<211> LENGTH: 241
<212> TYPE: PRT
<213> ORGANISM: Artificial Sequence
<220> FEATURE:
<223> OTHER INFORMATION: A modified protein of the present application

<400> SEQUENCE: 2

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Gly Gly Gly Tyr Asn Ser His Asn Val Tyr Ile Met Ala Asp Lys Gln
145                 150                 155                 160

Lys Asn Gly Ile Lys Val Asn Phe Lys Ile Arg His Asn Ile Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Tyr Gln Ser
        195                 200                 205

Ala Leu Ser Lys Asp Pro Asn Glu Lys Arg Asp His Met Val Leu Leu
    210                 215                 220

Glu Phe Val Thr Ala Ala Gly Ile Thr Leu Gly Met Asp Glu Leu Tyr
225                 230                 235                 240

Lys
```

<210> SEQ ID NO 3
<211> LENGTH: 6

<212> TYPE: PRT
<213> ORGANISM: Artificial Sequence
<220> FEATURE:
<223> OTHER INFORMATION: Peptide-Linker

<400> SEQUENCE: 3

Gly Gly Thr Gly Gly Ser
1               5

<210> SEQ ID NO 4
<211> LENGTH: 12
<212> TYPE: PRT
<213> ORGANISM: Artificial Sequence
<220> FEATURE:
<223> OTHER INFORMATION: Peptide-Linker

<400> SEQUENCE: 4

Gly Gly Thr Gly Gly Ser Gly Gly Thr Gly Gly Ser
1               5                   10

<210> SEQ ID NO 5
<211> LENGTH: 8
<212> TYPE: PRT
<213> ORGANISM: Artificial Sequence
<220> FEATURE:
<223> OTHER INFORMATION: FLAG tag

<400> SEQUENCE: 5

Asp Tyr Lys Asp Asp Asp Asp Lys
1               5

<210> SEQ ID NO 6
<211> LENGTH: 238
<212> TYPE: PRT
<213> ORGANISM: Aequorea victoria

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ala Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

```
Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 7
<211> LENGTH: 238
<212> TYPE: PRT
<213> ORGANISM: Artificial Sequence
<220> FEATURE:
<223> OTHER INFORMATION: CFP [cyan flruorescent protein]

<400> SEQUENCE: 7

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Ala Trp Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile His Phe Gln Asp Asp Gly Lys Tyr Lys Thr Arg Gly Glu Val
            100                 105                 110

Lys Phe Glu Gly Asp Thr Leu Val Asn Arg Val Glu Leu Lys Gly Glu
        115                 120                 125

Gly Phe Lys Glu Asp Gly Asn Ile Leu Gly His Lys Leu Glu Tyr Ser
130                 135                 140

Ala Ile Ser Asp Asn Val Tyr Ile Met Pro Asp Lys Ala Asn Asn Gly
145                 150                 155                 160

Leu Glu Ala Asn Phe Lys Ile Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Cys Gln Ser Ala Ile Ser
        195                 200                 205

Lys Asp Arg Asn Glu Ala Arg Asp His Met Val Leu Leu Glu Ser Phe
    210                 215                 220

Ser Ala Tyr Cys His Thr His Gly Met Asp Glu Leu Tyr Arg
225                 230                 235
```